US006855833B2

(12) United States Patent
Kanter et al.

(10) Patent No.: US 6,855,833 B2
(45) Date of Patent: Feb. 15, 2005

(54) METHODS FOR PRODUCING AMINO SUBSTITUTED CHROMANES AND INTERMEDIATES THEREOF

(75) Inventors: James Kanter, South San Francisco, CA (US); John J. G. Mullins, S. F., CA (US); Robert Scarborough, Half Moon Bay, CA (US); Derek Walker, Summit, NJ (US); Thomas Hense, Recklinghausen (DE)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 7 days.

(21) Appl. No.: 10/296,873

(22) PCT Filed: Jun. 1, 2001

(86) PCT No.: PCT/US01/17688

§ 371 (c)(1),
(2), (4) Date: Aug. 25, 2003

(87) PCT Pub. No.: WO01/94330

PCT Pub. Date: Dec. 13, 2001

(65) Prior Publication Data

US 2004/0225137 A1 Nov. 11, 2004

Related U.S. Application Data

(60) Provisional application No. 60/208,771, filed on Jun. 2, 2000, and provisional application No. 60/208,843, filed on Jun. 2, 2000.

(51) Int. Cl.$^7$ .............................................. C07D 311/66
(52) U.S. Cl. ...................................... 549/404; 549/407
(58) Field of Search .................................. 549/404, 407

(56) References Cited

U.S. PATENT DOCUMENTS 5,861,304 A    1/1999    Holla et al.

OTHER PUBLICATIONS

M. J. Fisher, et al., "Fused Bicyclic Gly–Asp β–Turn Mimics with Specific Affinity for GPIIb–IIIa," Journal of Medicinal Chemistry, vol. 42, No. 23, 1999, pp. 4875–4889.
Wulff, et al., Über die Eignung Verschiedener Aldehyde und Ketone als Haftgruppen für Monoalkohole, Chem Ber., 119, 1876–1889 (1986), XP001037635.
Buehler, et al., "2–Hydroxy–5–Nitrobenzyl Chloride," Org., Synth., vol. 20, 1940, pp. 59–61.
T. Inoue, et al., "A New Synthesis of o–Quinonemethides and Their Inter–and Intramolecular Cyclization Reactions," Bull. Chem. Soc. Jpn, vol. 63, pp. 1062–1068 (1990).

Primary Examiner—Taofiq Solola
(74) Attorney, Agent, or Firm—Knobbe, Martens, Olson & Bear LLP

(57) ABSTRACT

Disclosed are processes for producing chromane compounds, preferably chroman-2-yl acetic acid compounds and 6-amino-chroman-2-yl acetic acid esters which are intermediates for producing platelet aggregation inhibitors and/or are themselves potent platelet aggregation inhibitors.

21 Claims, No Drawings

METHODS FOR PRODUCING AMINO SUBSTITUTED CHROMANES AND INTERMEDIATES THEREOF

This is the U.S. national phase under 35 U.S.C. § 371 of International application PCT/US01/17688, published in English, filed Jun. 1, 2001, which claims priority to U.S. Provisional Application Nos. 60/208,771, filed Jun. 2, 2000; and 60/208,843, filed Jun. 2, 2000.

FIELD OF THE INVENTION

This invention relates to processes for producing chromane compounds, preferably chroman-2-yl acetic acid compounds and amino substituted chroman-2-yl acetic acid esters which are intermediates for producing platelet aggregation inhibitors and/or are themselves potent platelet aggregation inhibitors.

BACKGROUND OF THE INVENTION

One process for making chromanes from coumarin derivatives is described in U.S. Pat. No. 5,731,324 at columns 101–103. However, that process involves chromatography as a purification step, which does not scale well commercially. The unprotected amino derivative bicyclic compound ethyl 2-(6-amino-chroman-2-yl)acetate is described on column 147. In view of the lack of scalability of the prior art process, there is a need for improved processes for producing compounds that are useful as intermediates in processes for producing platelet aggregation inhibitors.

SUMMARY OF THE INVENTION

In accordance with one preferred embodiment, there is provided a process for making a compound according to the formula

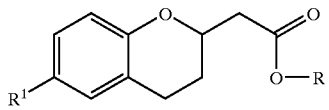

wherein R is H or an alkyl group, and $R^1$ is an amino group, an amino with a protecting group, or a nitro group. The process comprises (a) through (d) as follows:
(a) reacting a compound of the formula:

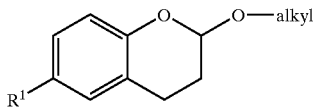

with a base under anhydrous conditions followed by adding a proton donor to produce a 2-hydroxy chromane compound of the formula:

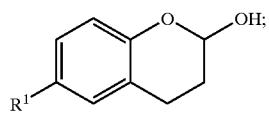

(b) condensing the hydroxychromane compound of (a) with a nucleophilic carbon species to afford the acetate compound as follows:

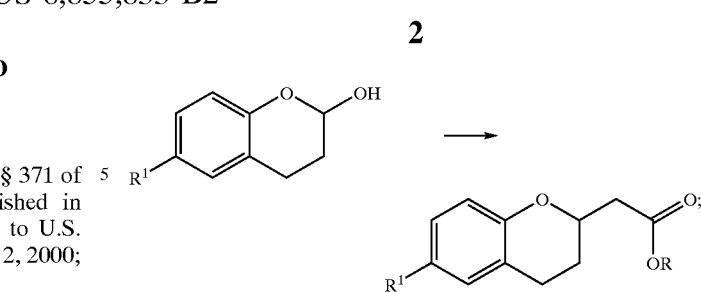

(c) optionally hydrogenating the nitro group or removing the protecting group from the amino group and forming a salt of the 6-amino group thereof; and
(d) optionally removing the alkyl group from the ester.

In preferred embodiments, the reagents for the foregoing process comprise one or more of the following: the base in (a) is sodium alkoxide or potassium alkoxide; the proton donor in (a) is water or a mineral acid; and the nucleophilic carbon species in (b) is a phosphorus ylide, preferably (carbethoxymethylene)triphenylphosphine, and (b) is run in an anhydrous solvent in the presence of base.

In a preferred embodiment, the foregoing process is used to make a compound according to the formula:

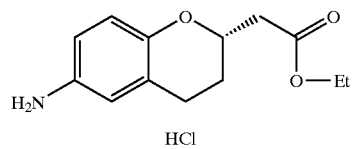

in greater than 95% enantiomeric purity with respect to the corresponding (2R) enantiomer. Such a process preferably comprises the following additional steps:
(e) resolving the racemate; and
(f) forming the hydrochloride salt of the resolved amine compound.

In a preferred embodiment, the starting material for the foregoing process:

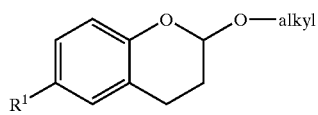

wherein $R^1$ is an amino group, an amino group with a protecting group, or a nitro group, is made according to the following process:
(i) reacting a compound of the formula:

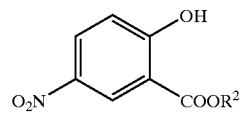

wherein $R^2$ is hydrogen or alkyl, with a reducing agent to produce a compound of the formula:

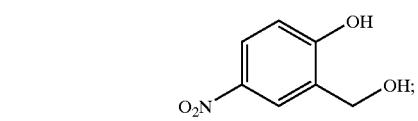

(ii) halogenating the hydroxyl group of the hydroxymethyl group; and (iii) condensing the compound of step (ii) with an alkylvinyl ether, therby making a compound of the formula:

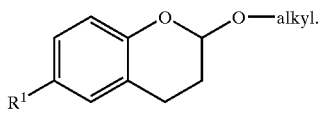

In a preferred embodiments, the reducing agent of step (i) is lithium aluminum hydride, sodium borohydride, borane, 9-BBN, or DIBAL-H, the reagent to perform the halogenation of step (ii) is thionyl chloride, and/or the alkylvinyl ether is ethylvinyl ether.

In a preferred embodiment, the starting material for the foregoing process:

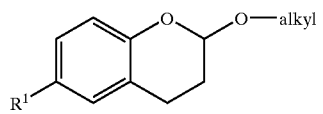

wherein $R^1$ is an amino group, an amino group with a protecting group, or a nitro group, is made according to the following process:
(i) reacting a compound of the formula:

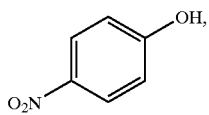

with formaldehyde, dimethylacetal, and hydrochloric acid to form a compound of the formula:

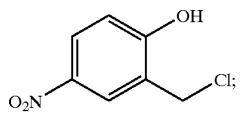

(ii) condensing the compound of step j) with an alkylvinyl ether to make a compound of the formula:

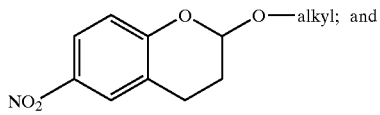

(iii) optionally hydrogenating the nitro group to form an amino group and adding a protecting group to the resulting amino group.

DETAILED DESCRIPTION OF THE PREFERRED EMBODIMENTS

As noted above, there is a need for improved processes for producing compounds that are useful as intermediates in processes for producing platelet aggregation inhibitors. There is a particular need for improved processes for making compounds having the benzene ring of the chromane substituted by an amino group or a protected amino group. Such intermediates are useful for coupling with a carbonyl group to produce a carboxamide link that results in compounds that are useful platelet aggregation inhibitors or in intermediates for forming platelet aggregation inhibitors. Also needed is a process to produce, in a relatively inexpensive manner, large quantities of chromane intermediates that are useful for being resolved by conventional processes to produce benzopyran or chromane derivatives wherein the chiral center at the two position of the saturated pyran ring portion of the bicyclic ring structure can be resolved into racemic mixtures (R/S) that are enriched with one of the R or S enantiomers, or to produce substantially pure compositions of a single enantiomer (R or S enantiomer). Due to inherent losses of up to 50% or more of the starting materials (assuming a 50/50 R/S racemate) during enantiomeric resolution, there is a need for a process which is efficient enough to be scaled to an industrial level for inexpensively producing large quantities of a desired intermediate compound or large quantities of final chroman-2-yl acetic acid ester compounds that are useful in the anticoagulant field.

Accordingly, there continues to be a need for a process that is adaptable to commercially scaleable production of such benzopyran derivatives. One or more of the foregoing needs may be met using the processes described herein and the compounds and intermediates made thereby.

Disclosed herein are processes for producing chromane compounds, preferably chroman-2-yl acetic acid compounds and amino substituted chroman-2-yl acetic acid esters which are intermediates for producing therapeutic agents, or are themselves therapeutic agents, for disease states in mammals that have disorders caused by or impacted by platelet dependent narrowing of the blood supply.

In one preferred embodiment, a 6-nitro-2-hydroxychromane compound is produced from a 2-hydroxymethyl-4-nitrophenol. The 2-hydroxymethyl-4-nitrophenol is readily obtained, e.g., by reducing 5-nitro-salicylic acid with a carboxylic acid reducing catalyst such as borane-THF, lithium tri-butoxyaluminohydride, lithium triethylborohydride, lithium trimethoxyaluminium hydride, and the like, preferably $LiAlH_4$ or borane-THF as follows:

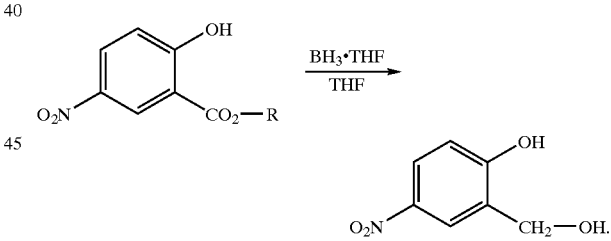

The 4-nitro-2-hydroxymethylphenol is then converted to a 2-halomethyl-4-nitrophenol via a mild halogenation reaction such as a thionyl chloride in THF or is produced directly from 4-nitrophenol in a solution of concentrated HCl, a catalytic amount of $H_2SO_4$ and formaldehyde dimethylacetal solution by bubbling gaseous HCl through the solution at about 50 to 80° C. (preferably 70° C.) until a thick white precipitate is formed. The thionyl chloride conversion of the 2-hydroxymethyl group is shown process is shown as follows:

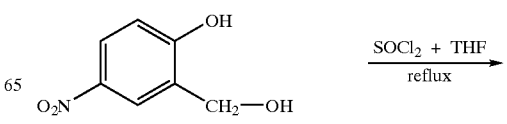

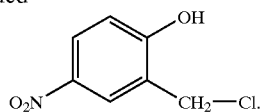

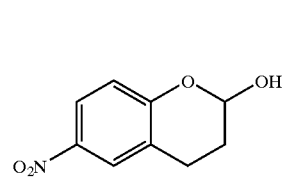

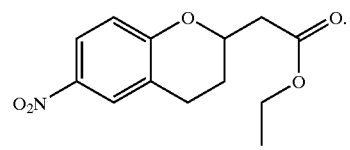

The 2-halo(e.g. chloro)methyl-4-nitrophenol is condensed to 2-ethoxy-6-nitrochromane by reacting the reacting the 2-halo(e.g. chloro)methyl-4-nitrophenol with 3-pentanone by dropwise addition of triethylamine. After the addition of the triethyl amine to the reaction mixture, the mixture is diluted by adding 3-pentanone and ethylvinylether and the mixture is heated to about 100° C. for about 6 hours, then cooled to about 0° C. and the precipitate filtered off to provide 2-ethoxy-6-nitrochromane, as follows:

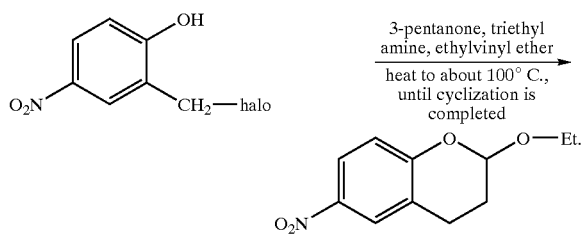

The 2-ethoxy-6-nitrochromane is converted to 6-nitro-2-hydroxychromane by a pseudo Wittig reaction, that is gradually rendered aqueous. In particular, the 2-ethoxy-6-nitrochromane is heated in the presence of a Wittig catalyst base such as sodium ethoxide or other similar metallic oxides in an anhydrous solvent such as toluene at about 50–100° C., preferably about 65–90° C., and more preferably about 80° C. to afford the acetate, and water or a dilute mineral acid such as HCl, HBr and the like is gradually added dropwise until a 1:1 molar equivalent of the water or acid has been added with respect to the 2-ethoxy-6-nitrochromane starting material, and additional water is added to assure conversion to the hydroxy group. The sodium ethoxide is neutralized with HCl and the reaction mixture is extracted with water. The organic layer is dried over magnesium sulfate to yield an anhydrous toluene/ethanol solution of the 2-ethoxy-6-nitrochromane compound.

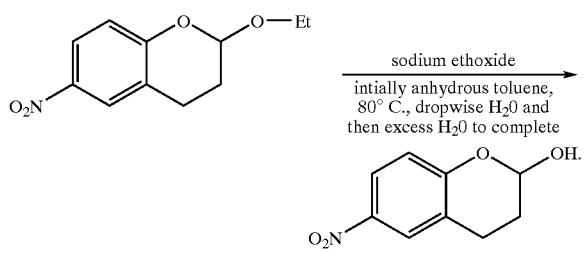

The 2-hydroxy-6-nitrochromane in the anhydrous toluene/ethanol solution (yielded anhydrous by drying above) is then condensed with a (carbemethoxymethylene)-triphenylphosphorane compound in the presence of a base such as sodium ethoxide in an acceptable solvent such as toluene at about 50–100° C., preferable about 65–90° C., and more preferably about 80° C. to afford the acetate. For example, as illustrated below:

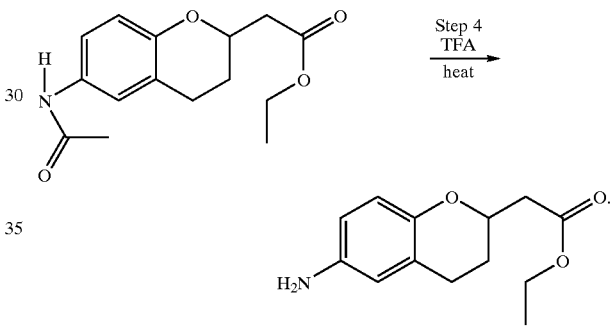

The racemic 6-nitrochroman-2-yl acetic acid (ethyl ester) can optionally be resolved into enriched compositions of the (2S>2R) or (2R>2S) enantiomers by hydrolysis with a lipase such as *Pseudomonas* lipase PS 30 and the like.

The nitro group can be reduced to an amino group by procedures that are standard in the art, such as $H_2$ and 5–10% Pd/C 5–10% or hydrogenation with hydrogen gas in the presence of other hydrogen catalysts, e.g., tin chloride an the like. If a protecting group or acetamido group is formed on the amine group during hydrogenation, it can optionally be removed with an acceptable acid such as trifluoroacetic acid at about 40–80° C., preferably 50–70° C., and more preferably about 60° C. to yield the free amine as follows:

If the 6-acetamidochroman-2-yl acetic acid (ethyl ester) (i.e. ethyl (6-acetamidochroman-2-yl)acetate) is a racemate, it can optionally be resolved into enriched compositions of the (2S>2R) or (2R>2S) enantiomers by hydrolysis prior to removing the protecting group. The free acid form can be selectively reacted with L-alaninol or D-alaninol to form a salt and the precipitate recrystallization. The enriched enantiomeric compositions after freeing of the D-alaninol or L-alaninol can be isolated, esterified and the 6-amino protecting group removed to produce enriched compositions of the (2S>2R) or (2R>2S) ethyl (6-aminochroman-2-yl) acetate enantiomers for coupling with a nitrile/carbonyl derivative as described in U.S. Pat. No. 5,731,324 at the example bridging pages 147 and 145 to produce an enriched enantiomeric platelet aggregation inhibitor. Other carbonyl derivatives described in the U.S. Pat. No. 5,731,324 patent may also be reacted with the chiral amine to produce enriched enantiomeric platelet aggregation inhibitors.

While an ethyl group was used to form the ester of the acetic acid side chain, the ethyl group can be replaced by H or another esterifying group selected from lower alkyl, lower alkenyl, lower alkynyl, phenyl, cinnamyl or other ester groups.

In either event, the protected amine benzopyran compound or the free amine benzopyran compound can be coupled to a cyanobenzoyl chloride group as described on pages 147 and 148 of U.S. Pat. No. 5,731,324, for example The ester group of the acetic acid side chain can be optionally changed, before of after the coupling step.

Further, the above process can be modified to produce a formyl, propyl or butyl side chain or the like, by utilizing a different triphenylphosphorane starting material.

The above discussion is a general description of preferred processes. The non-limiting illustrative schemes are set forth below, show additional preferred embodiments.

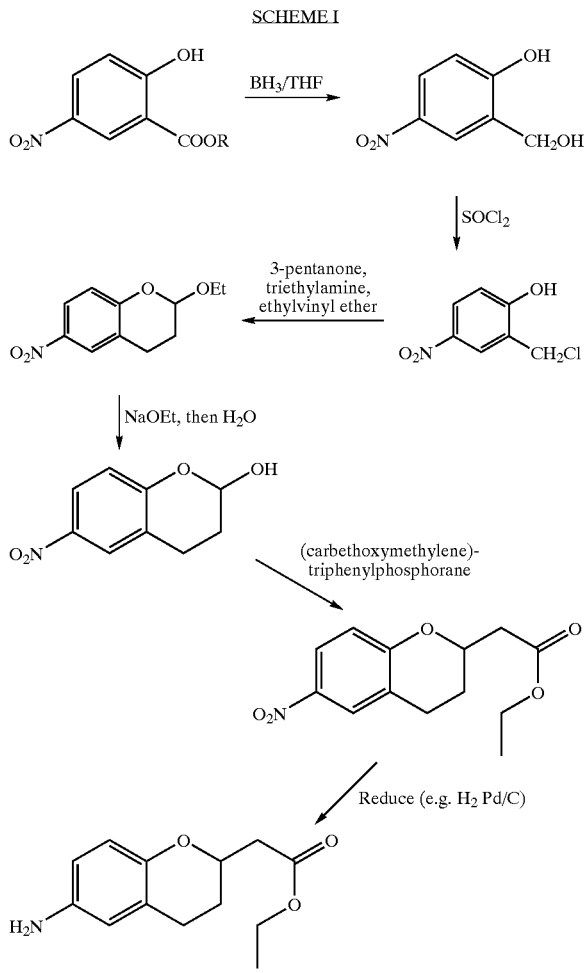

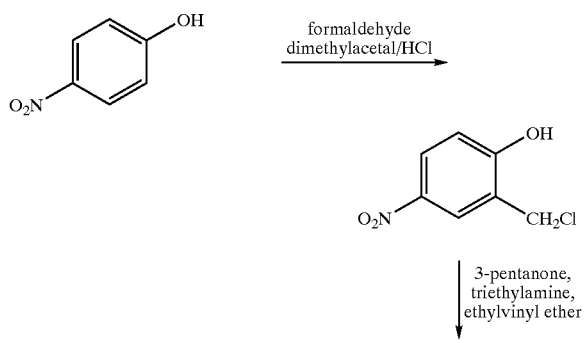

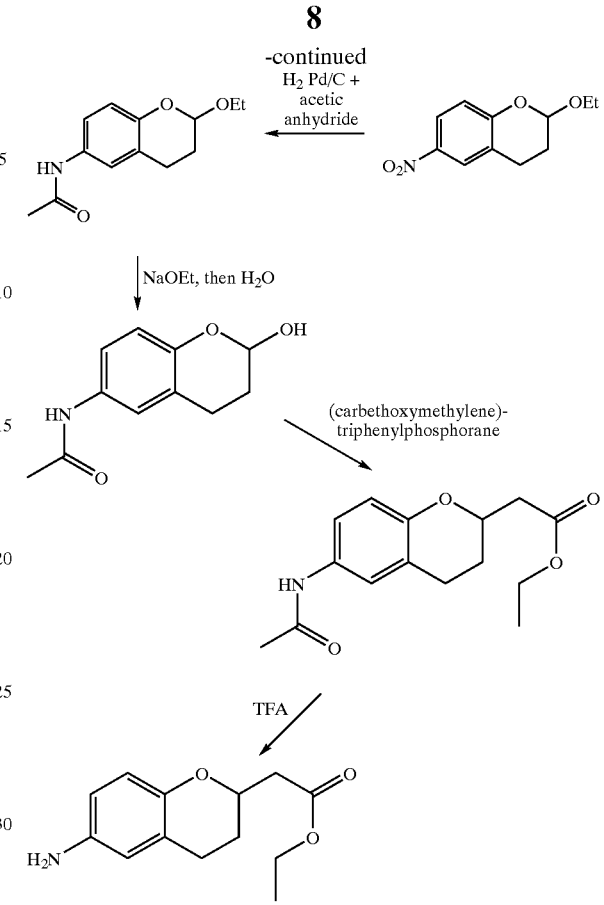

Additionally, reagents and conditions having similar results may be substituted for those disclosed. For reactions producing racemates, resolution of the racemate may occur at any suitable place in the scheme and may proceed with reagents other than lipase, a preferred reagent and process disclosed herein. Furthermore, salts and esters may be formed and/or interconverted with the corresponding free acid or base as desired at any place in the scheme if desired, such as to aid in isolation or purification of a compound or intermediate.

In other embodiments, the order of some of the reactions in the schemes may be changed, and additional steps of protecting, deprotecting, nitrating, hydrolyzing, esterifying, and the like may be added to the schemes at various points. Such minor alterations are within the scope of the disclosure herein. Although the esters shown are primarily ethyl esters, other esters may be made, either by use of different solvents and/or reagents in the initial formation reactions or by transesterification.

The starting materials used in the disclosed processes are commercially available from chemical vendors such as Aldrich, Lancaster, TCI, Bachem Biosciences, and the like, or may be readily synthesized by known procedures including those present in the chemical literature, or may be made by using procedures such as indicated above.

Reactions are carried out in standard laboratory glassware and reaction vessels under reaction conditions of standard temperature and pressure, except where it is otherwise indicated, or where use of non-STP conditions for a procedure is known in the art. Some procedures, reactions, and/or workups which are well known in the art or which are readily available in standard reference texts in the art, including Beilstein and Fieser and Fieser, may not be presented herein owing to their stature of being within the knowledge of one of ordinary skill. Further, the processes disclosed herein may be carried out on a commercial scale by utilizing reactors and standard scale-up equipment available in the art for producing large amounts of compounds in the commercial environment. Such equipment and scale-up procedures are known to the ordinary practitioner in the field of commercial chemical production.

During the synthesis of these compounds, amino or acid functional groups may be protected by blocking groups to prevent undesired reactions with the amino group during certain procedures. Procedures for such protection and removal of protecting groups are routine and well known to the ordinary practitioner in this field.

Enantiomeric Resolution and Acid Salt Formation

When a reaction results in the production of racemic chroman-2-yl carboxylic acids and esters or their derivatives and/or intermediates, these racemates are preferably resolved to produce a mixture enriched in one of the R or S enantiomers or resolved into a substantially pure composition of one of the enantiomers. Examples of processes for resolving the racemic mixtures are provided herein and others are known to those skilled in the art. Additionally, processes for the formation of acid addition salts such as the hydrochloride salt of the 6-position amino acid group on the chromane nucleus are known in the art. Other such salts are also envisioned.

As noted above, in preferred aspects, the methods disclosed herein relate to processes for producing amidino-substituted benzoyl compounds, wherein the phenyl ring may be substituted with lower alkyl, lower alkoxy, Cl, F, Br, I, and the like, which are intermediates for coupling with bicyclic compounds to produce therapeutic agents, or are themselves therapeutic agents, for disease states in mammals that have disorders caused by or impacted by platelet dependent narrowing of the blood supply. Some of such methods disclosed herein include processes for producing racemic amino substituted bicyclic compounds such as racemic, 6-amino-chroman-2-yl acetic acid esters, and resolving such bicyclic compounds into either the R or S enantiomer.

In a preferred aspect, racemic nitro substituted compounds having the bicyclic structures described below, are enzymatically resolved into an enantiomerically rich composition (2R>2S) or (2S>2R). Such resolution is preferably performed using a chirally selective *Pseudomonas* lipase such PS 30, or a stabilized lipase (glutarate stabilized, for example) such as the Altus, Inc. ChiroCLEC-PC lipase, or the like, may be utilized to resolve the nitro-substituted chromane, hydroxy chromane, or oxo-chromane compounds and the like.

One preferred resolution process for a chromane is as follows:

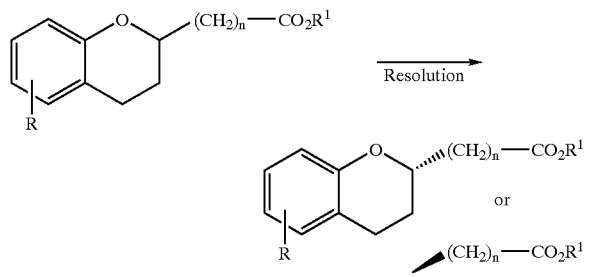

wherein R is a nitro or other electron withdrawing group on the phenyl or benzene ring such as an oxime or halogen group and $R^1$ is hydrogen or the alkyl core of an alcohol group which can form an ester, such as a methylene or ethylene group from methanol or ethanol and n is 0 to 6. Preferably, the 2-carboxylic acid group is esterified with a methyl or ethyl group and the R group on the phenyl portion is a member selected from the group consisting of $NO_2$, halogen, an oxime derivative or the like. More preferably, R group is an 6-nitro group.

In a preferred aspect, PS 30 from *Pseudomonas* is used to selectively hydrolyze a 2-acyl ester group, or to catalyze selectively esterifying the free acid. When PS-30 is used, the S-enantiomer is selectively hydrolyzed and in an aqueous basic/organic solvent can be extracted in the aqueous layer as a basic salt. The aqueous solution can then be neutralized to obtain the free acid. Alternatively, the organic portion of the aqueous/organic solvent extraction is enriched in the R-enantiomer which can then be recovered by heating in a base to form a basic salt that precipitates from the organic solvent. The yield is about 40–50% of 95% or greater purity of the desired crude enantiomer. Essentially 100% pure single enantiomer can be obtained from the 95% or greater crude enantiomer by refluxing the crude enantiomer in methanol. The amount of methanol solvent utilized in the desired purification reflux step can be varied to produce optimum yields of the desired pure enantiomer.

Where resolution of a 6-amino-chroman-2-yl acid (or an acid derivative) or other bicyclic structures that are substituted by an amino group is desired, although the process may proceed with the amino group, the process preferably first proceeds by oxidation of the amino group to a more electron withdrawing nitro group. Alternatively, the reaction is begun with a nitro-substituted material or a protected amino group. Preferably, the amino-compound is reacted with an oxygen source, including but not limited to, $O_2$, ozone, or $H_2O_2$, optionally in the presence of a catalyst such as a metal oxide catalyst selected from the group consisting of tungstate, molybdate and vanadate to result in oxidation of the amino group. In one preferred embodiment, an effective amount of hydrogen peroxide of from about 1–10, more preferably 1–5 moles of hydrogen peroxide per mole of amino groups is used in an aqueous or partially aqueous solution of a lower alcohol solvent to convert the ring amino group to a nitro group as follows:

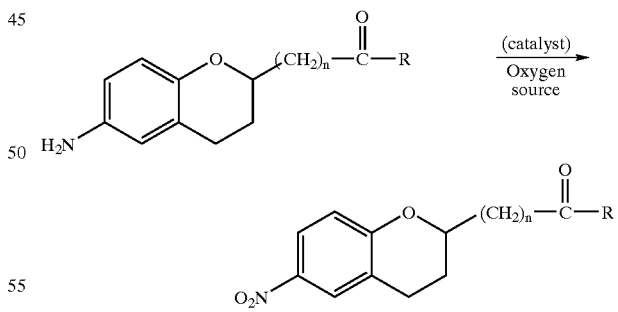

R is preferably hydroxy, alkoxy or amino.

In a preferred aspect, the oxidation of the amino to a nitro group is carried out at a temperature from about 20° C. to about 100° C., preferably from about 40° C. to about 85° C., more preferably from about 55° C. to about 75° C., and most preferably at about 60° C.

In a preferred aspect, the oxygenation catalyst for the amino to nitro conversion is a metal oxide catalyst selected from the group consisting of tungstate, molybdate and vanadate. Examples of tungstate or water soluble quaternary ammonium tungstates include tungstic acid (H₂WO₄), tungsten trioxide (WO₃), tungstenic acid (H₂WO₄), sodium tungstate (Na₂WO₄), potassium tungstate (K₂WO₄), and mixtures thereof. The corresponding molydbates, MoO₃, H₂MoO₄, K₂MoO₄, Na₂MoO₄, and mixtures thereof, and the corresponding vanadates Va₂O₅, HVO₃, KVO₃, NaVO₃, and mixtures thereof may be utilized. The catalyst is typically present at a level of from 0.001% to 2%, preferably 0.01% to 1% and more preferably from 0.05% to 0.5%, by weight of the aqueous or partially aqueous solution.

A chelating agent or heavy metal ion sequestrant such as organic phosphonates, EDTA (ethylene diamine tetra-acetic acid) and the like, may be utilized during the oxidation reaction, preferably diethylenetriamine penta(methylene phosphonate) ("DTPMP"). Such complexes are described in U.S. Pat. No. 4,259,200. The preferred concentration of sequestrant is approximately a 1:1 ratio to the metal catalyst ions utilized.

In a preferred aspect, the mixture is resolved by using an enantiomerically selective ester hydrolyzing agent such as a lipase, preferably a *Pseudomonas* lipase, most preferably PS 30 or a glutarate stabilized version (for example ChiroCLEC-PC lipase for Altus, Inc.). In a preferred embodiment the selective hydrolysis by the lipase is conducted in an aqueous basic solution (preferably a buffer solution) with lipase PS 30. In this process, the insoluble ester racemate is agitated with stirring and the hydrolyzed acid forms a salt that is soluble in the aqueous solution. The solution can be filtered and the hydrolyzed acid (2S) can be recovered from the aqueous solution by neutralizing the solution to reform the water-insoluble free acid from the salt and thus recover the insoluble free acid as a precipitate. Rinsing this precipitate with water will yield the (2S) enantiomer free acid. The lipase biomass and the enriched (2R) enantiomer are preferably recovered by rinsing the biomass with an appropriate solvent such as ethyl acetate, filtering the ethyl acetate solvent and evaporating the solvent to recover the enriched (2R) enantiomer.

Depending upon whether the desired enantiomer is the (2S) or the (2R) enantiomer, the less desired enantiomer can be recycled by using a racemization step followed by exposure of the resulting racemate to the lipase to obtain more of the desired (2S) or (2R) enantiomer and increase the overall yield of the process. The formation of a racemate from a single enantiomer is preferably accomplished by exposing the enantiomer to a basic alcoholic solution such as a sodium or potassium ethanolate solution in the corresponding alcohol or an inert solvent. Other procedures which open the ring at the ring oxygen of the chromane and then reclose it may also be utilized to produce a racemate from a single enantiomer. By repeating the resolution and racemate forming steps a higher overall yield may be obtained. The racemate forming step may be illustrated in a preferred compound as follows:

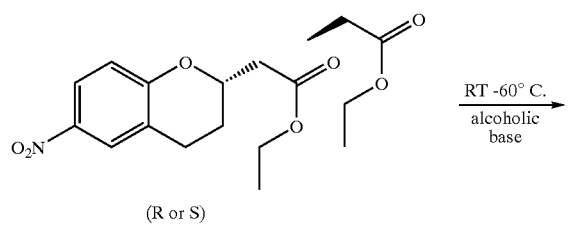

(R or S)

-continued

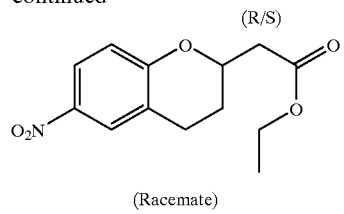

(Racemate)

wherein, as illustrated, a catalytic amount of sodium ethoxide, potassium ethoxide or similar catalytic base in R¹OH (preferably EtOH) is utilized until racemization is completed, usually for 4–8 hours at about 45° C. (longer at room temperature). After acidification with an acid such as 1N HCl (preferably acetic acid) to quench the base and form a soluble salt with the base, the reaction mixture containing the racemic acid mixture is mixed with a greater volume of water than the volume of the alcohol solvent to render the ethyl ester of the racemic (2R/2S) 6-nitro-chroman-2-yl acetic acid insoluble. The racemic mixture is collected as a precipitate by filtration and is rinsed with water. Optionally, the crude product can be thoroughly rinsed with water and recrystallized in an appropriate solvent to ensure that the sodium or potassium ions are removed from the racemate. The resulting ester racemate can then be recycled by exposure to the lipase to obtain a higher yield of the desired single enantiomer with respect to the initial amount of racemate starting material.

Uses of Compounds

As mentioned above, the compounds produced according to preferred embodiments find utility as intermediates for producing therapeutic agents or as therapeutic agents for disease states in mammals, including those which have disorders that are due to platelet dependent narrowing of the blood vessels; such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, anastomosis of vascular grafts, and etc. These conditions represent a variety of disorders thought to be initiated by platelet activation on vessel walls.

Platelet adhesion and aggregation is believed to be an important part of thrombus formation. This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin, the GP IIb/IIIa binding site becomes available to fibrinogen, eventually resulting in platelet aggregation and clot formation. Thus, intermediate compounds for producing compounds that effective in the inhibition of platelet aggregation and reduction of the incidence of clot formation are useful intermediate compounds.

The compounds produced according to preferred embodiments may also be used as intermediates to form compounds that may be administered in combination or concert with other therapeutic or diagnostic agents. In certain preferred embodiments, the compounds produced by coupling preferred compounds produced herein with benzoyl halide derivatives may be co-administered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds produced from the intermediates may act in a synergistic fashion to prevent reocclusion following a successful thrombolytic therapy and/or reduce the time to reperfusion. Such compounds may also allow for reduced doses of the thrombolytic agents to be used and therefore minimize potential hemorrhagic side-effects. Such compounds can be utilized in vivo, ordinarily in mammals such as primates, (e.g. humans), sheep, horses, cattle, pigs, dogs, cats, rats and mice, or in vitro.

Coupling Reaction of the Hydrochloride Salt Intermediate Compounds

The above compounds produced according to preferred methods may be isolated and further reacted to substitute a desired group for one or more of the hydrogen atoms on the amino group by a coupling reaction. Particularly preferred is a coupling reaction of the amino group with an acyl halide compound. For example, compounds such as 5-amidino-thiophen-2-yl carboxylic acid derivatives (or an acyl halide such as the acyl chloride) and 4-amidinobenzoyl chloride may be coupled to ethyl (2S)-(6-aminochroman-2-yl)acetate (or its hydrochloride salt) to form ethyl (2S)-[6-(5-amidino-2-thiophenoyl)amino-chroman-2-yl]acetate and ethyl (2S){6-[(4-amidinophenyl)carbonylamino]chroman-2-yl}acetate, or other similar compounds or their derivatives which are known platelet aggregation inhibitors. For examples of such platelet aggregation inhibitors, see U.S. Pat. No. 5,731,324. The ring portion of the above amidino-aroyl or amidino-heteroaroyl derivatives may be substituted by groups such as methyl, ethyl, fluoro, iodo, bromo, chloro, methoxy, ethyoxy, and the like which results in compounds that are known platelet aggregation inhibitors. Standard coupling procedures may be utilized, but procedures utilizing reaction mixtures the compounds, in salt form, are suspended in solvents such as acetonitrile, toluene, or the like, are preferred.

The compound formed from the coupling reaction may be used as either the salt or the free base, and may be readily interconverted between the two forms by using procedures which include those known in the art as well as reacting the compound with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt, or one salt form of the product may be converted to another using the same general process. The free base or salts may be purified by various techniques such as recrystallization in a lower alkanol such as methanol, ethanol, propanol, isopropanol and the like, for example, or a mixture thereof. In preferred embodiments, the compound is recovered as the hydrochloride salt and the recrystallization solvent is a 90/10–10/90 mixture of ethanol and isopropanol. Non-toxic and physiologically compatible salts are preferred, although other types of salts may also be used, such as in the processes of isolation and purification.

Compositions and Formulations

Diagnostic and therapeutic applications of the compounds formed by procedures disclosed herein, including the aforementioned coupling reactions, will typically utilize formulations wherein the compound, or a pharmaceutically acceptable salt, solvate, or prodrug, is combined with one or more adjuvants, excipients, solvents, or carriers. The formulations may exist in forms including, but not limited to tablets, capsules or elixirs for oral administration; suppositories; sterile solutions or suspensions for injectable or parenteral administration; or incorporated into shaped articles. Subjects in need of treatment (typically mammalian) using the compounds produced according to preferred embodiments herein and/or produced by coupling such compounds with other compounds, including benzoyl halide derivatives can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations are prepared for storage or administration by mixing the compound, or a pharmaceutically acceptable salt, solvate or prodrug thereof, having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counter ions such as sodium and/or nonionic surfactants such as Tween, Pluronics or polyethyleneglycol.

Dosage formulations to be used for parenteral administration are preferably sterile. Sterility is readily accomplished by filtration through sterile membranes such as 0.2 micron membranes, or by other conventional methods known to those skilled in the art. Formulations are preferably stored in lyophilized form or as an aqueous solution. The pH of such preparations are preferably between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds are desirably incorporated into shaped articles such as implants which may employ inert materials such as biodegradable polymers or synthetic silicones, for example, Silastic, silicone rubber or other polymers commercially available.

The compounds may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds may also be delivered by the use of antibodies, antibody fragments, growth factors, hormones, or other targeting moieties, to which the compound molecules are coupled. The compounds may also be coupled with suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the platelet aggregation inhibitors may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound and formulation, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds or formulations may be administered several times daily, in a once daily dose, or in other dosage regimens.

Typically, about 0.5 to 500 mg of a compound or mixture of compounds, as the free acid or base form or as a pharmaceutically acceptable salt or prodrug derivative (including esters), is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

The compounds and formulations may be used alone or in combination, or in combination with other therapeutic or diagnostic agents. In certain preferred embodiments, the compounds and/or formulations may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds and formulations can be utilized in vivo, ordinarily in mammals such as primates, such as humans, sheep, horses, cattle, pigs, dogs, cats, rats and mice, or in vitro.

The compounds, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboanginitis iobliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Without further description, it is believed that one of ordinary skill in the art can, using the preceding description and the following illustrative examples, make and utilize the compounds disclosed herein and practice the claimed methods. The following working examples therefore, specifically point out preferred embodiments, and are not to be construed as limiting in any way the remainder of the disclosure.

EXAMPLES

Example 1

Production of 2-hydroxymethyl-4-nitrophenol

To a $BH_3.THF$ solution (110 mL, 1M, 110 mmoles) was added dropwise a solution of 5-nitro-salicylic acid (10.0 g, 54.6 mmoles) in 930 mL THF. After a few milliliters, the reaction mixture was cooled with ice to maintain a temperature of about 15° C. The clear brown solution was warmed to room temperature and stirred for an additional 7 hours. During this time a precipitate formed. $BH_3.THF$ (20 ml, 20 mmoles) was added and stirring was continued overnight.

The mixture was cooled to 5° C. and carefully hydrolyzed with 1 M HCl (100 mL). Methyl tert-butyl ether (MTBE) (100 mL) was added, the phases were separated and the aqueous layer was extracted with MTBE (2×70 mL). The combined organic layers were dried over $MgSO_4$ (10 g), filtered and evaporated to give 10.5 g of a pale ochre solid. This solid was recrystallized from 65 mL toluene to give 7.033 g (76%) of 2-hydroxymethyl-4-nitrophenol as a pale ochre solid.

$^1$H-NMR (300 MHz, DMSO) δ=4.67 (s, 2H), 4.89 (s, 1H), 6.87 (d, 1H, J=8.9Hz), 8.04 (dd, 1H, J=8.9 Hz, 2.9 Hz), 8.27 (d, 1H, J=8.9 Hz, 2.9 Hz).

MS (API-ES negative) m/Z=168 (M−H)⁻.

Example 2

Production of 2-chloromethyl-4-nitrophenol

The 2-hydroxymethyl-4-nitrophenol of Example 1 was added to a reaction flask with 200 mL of THF under nitrogen with stirring and heated to reflux while being vented to a scrubber system for efficient removal of HCl and $SO_2$ gases which are eliminated. Thionyl chloride was slowly added dropwise with stirring, and the reaction was monitored with HPLC to indicate when halogenation of the hydroxymethyl group was complete (about 12 hours). The THF solvent was evaporated under vacuum and dried overnight to provide a yellow powder of substantially pure 2-chloromethyl-4-nitrophenol (about 95% yield).

$^1$H-NMR (300 MHz, $CDCl_3$) δ=4.67 (s, 2H), 7.01 (d, 1H, J=8.9 Hz), 8.05 (dd, 1H, J=2.8 Hz), 8.23 (d, 1H, J=2.8 Hz).

Example 3

Production of 2-chloromethyl-4-nitrophenol

A 5-necked flask equipped with mechanical overhead stirrer, gas inlet tube, reflux condenser and a thermometer was charged with 4-nitrophenol (100 g, 0.72 mol). Concentrated HCl 932%, 1.3 L), conc. $H_2SO_4$ (98%, 10 mL) and formaldehyde dimethylacetal (152.4 g, 2 moles) were added and the mixture was heated to 70° C. Gaseous HCl was bubbled through the mixture for 4 hours. During this time a thick white precipitate formed. The suspension was cooled to 0° C., the precipitate was isolated by vacuum filtration and the yellow powder was dried over night under vacuum to give 108.76 g of slightly impure 2-chloromethyl-4-nitrophenol (about 76% yield).

$^1$H-NMR (300 MHz, $CDCl_3$) δ=4.67 (s, 2H), 7.01 (d, 1H, J=8.9 Hz), 8.05 (dd, 1H, J=2.8 Hz), 8.23 (d, 1H, J=2.8 Hz).

Example 4

Production of 2-ethoxy-6-nitrochromane 2 chloromethyl-4-nitrophenol (15.0 g, 80 mmoles) was dissolved in 3-pentanone (300 mL) and triethylamine (11.15 mL, 80.0 mmoles) was added dropwise. The yellow suspension was diluted with 3-pentanone (75 mL) and ethylvinylether (30.6 mL, 320.0 mmoles) was added in one portion. The mixture was heated to 100° C. for 6 hours, cooled to 0° C. and the precipitate was filtered off. After evaporation of the solvents under vacuum, 15.21 g (93 area % (GC, 79%) were obtained as an orange oil.

$^1$H-NMR (300 MHz, $CDCl_3$) δ=1.20 9t, 3H, J=7.1 Hz), 1.95 (dddd, 1H, J=2.6, 5.8, 8.4, 13.7 Hz,), 2.07–2.16 (m, 1H), 2.72 (ddd, 1H, J=3.5, 5.7, 16.5 Hz), 3.05 (ddd, 1H, J=5.9, 12.2, 16.5 Hz), 3.68 (dq, 1H, J=7.1, 9.7 Hz), 3.89 (dq, qH, J=7.1, 9.7 Hz), 5.34–5–536 (m, 1H), 6.87–6.90 (m, 1H), 7.98–8.02 (m, 2H).

$^{13}$C-NMR (75 MHz, $CDCl_3$) δ=15.1, 20.4, 25.9, 64.3, 97.7, 117.5, 123.3, 123.5, 125.4, 141.3, 158.0.

Example 5

Production of 2-ethoxy-6-acetamidochromane 2-ethoxy-6-nitrochromane (4.92 g, 21.1 mmoles) of Example 4 was dissolved in THF (50 mL) and the round bottom flask was purged with nitrogen gas. Pd/C (10%, 500 mg) was added, nitrogen replaced by hydrogen using a balloon, and acetic anhydride (4.65 g, 45.5 mmoles) was added in one portion. After 5 days of stirring the mixture was filtered through celite and evaporated under vacuum to give 6.21 g of a brown oil. The residue was purified by $SiO_2$ chromatography (150 g, M column 7 cm, eluent EtOAc/heptane 2/1) to give 3.04 g (57%) 2-ethoxy-6-acetamidochromane as a pale brown solid.

$^1$H-NMR (300 MHz, $CDCl_3$) δ=1.18 (t, 3H, J=7.1 Hz), 1.89–2.05 (m, 2H), 2.13 (s, 3H), 2.6 (ddd, 1H, J=3.9, 5.8, 16.2 hz, 2.94 (ddd, 1H, J=6.1, 11.5, 16.2H), 3.62 (dq, 1H, J=7.1, 9.6 Hz), 3.86 (d1, 1H, j=7.1, 9.6 Hz) 5.21–5.17 (m, 1H), 6.75 (d, 1H, j=8.7 h), 7.10 (dd, 1H, J=2.6, 8.6H), 7.26 (d brs, 2×1H, J=0.6 Hz).

$^{13}$C-NMR (75 MHz, DMSO) δ=16.8, 21.9, 25.5, 27.7, 64.7, 98.0, 118.1, 120.5, 121.8, 123.9, 134.0, 149.4, 169.4.

MS (API-ES pos.): m/z=236 (M+H)⁺.

Example 6

Production of 2-hydroxy-6-nitrochromane

From Example 4, 15.0 g (about 80 mmoles) of 2-ethoxy-6-nitrochromane was dissolved in anhydrous toluene (300 mL) and 1.3 mg of sodium ethoxide was added with stirring. The reaction mixture was then heated to about 80° C. and stirred for about an hour, followed by slowly adding dropwise with stirring about 85 mmoles of anhydrous HCl. The evolution of the reaction was checked with TLC and HPLC. An additional amount of sodium ethoxide (3 mg) was added and the mixture was maintained at about 80° C. for 24 hours with stirring. After cooling the reaction mixture to room temperature, 500 mL of toluene and silica gel are added to the reaction medium. The mixture was stirred for about an hour at about 20° C. The silica gel was filtered and washed twice with 2×200 mL of toluene. The filtrate and the washes were pooled and the solvents were distilled off under reduced pressure (T<50° C.) until the residue comprised about 200 mL of a toluenic solution of 2-hydroxy-6-nitrochromane.

Example 7

Production of 2-hydroxy-6-acetamidochromane 3 g (about 12 mmoles) of 2-ethoxy-6-acetamidochromane was dissolved in anhydrous toluene (50 mL) and 250 micrograms of sodium ethoxide was added with stirring. The reaction mixture was then heated to about 80° C. and stirred for about an hour, followed by slowly adding dropwise with stirring about 13.5 mmoles of anhydrous HCl. The evolution of the reaction was checked with TLC and HPLC. An additional amount of sodium ethoxide (750 micrograms) was added and the mixture was maintained at about 80° C. for 24 hours with stirring. After cooling the reaction mixture to room temperature, 85 mL of toluene and silica gel were added to the reaction medium. The mixture was stirred for about an hour at about 20° C. The silica gel was filtered and washed twice with 2×30 mL of toluene. The filtrate and the washes were pooled and the solvents were distilled off under reduced pressure (T<50° C.) until the residue had a volume of about 60 mL of a toluenic solution of 2-hydroxy-6-acetamidochromane.

Example 8
Production of ethyl 2-(6-nitrochroman-2-yl)acetate

To the toluenic solution of Example 6, above, was added 9.8 g of (carbethoxymethylene)-triphenylphosphorane (85 mmole, corresponding to 1.1 equivalents of the amount of 6-nitro-2-ethoxychromane used as the initial starting material in Example 4) and 1.3 mg of sodium ethoxide and 100 mL of anhydrous toluene. The reaction mixture was then heated to about 80° C. and stirred at 80° C. for at least about 2 hours. The evolution of the reaction was then checked by TLC and HPLC. An additional amount of sodium ethoxide (3 mg) was added and the mixture was maintained at about 80° C. for about 24 hours with stirring. After cooling the reaction mixture to room temperature, silica gel and 500 mL of anhydrous toluene were added to the reaction medium which was stirred for at least 1 hour at about 20° C.

The silica gel was filtered and washed twice with 2×200 mL of toluene. The filtrate and the washes were pooled and the solvents were distilled off under reduced pressure (T≦50° C.) until the residue solution had a volume of about 150 mL. The residue was cooled down to about 25° C. to result in 150 mL toluenic solution of ethyl 2-(6-nitrochroman-2-yl)acetate.

Example 9
Production of ethyl 2-(6-acetamidochroman-2-yl)acetate

To a toluenic solution of the material produced in Example 7, above, was added 1.7 g of (carbethoxymethylene)-triphenylphosphorane (12 mmole, corresponding to 1.1 equivalents of the amount of 6-acetamido-2-ethoxychromane used as the initial starting material in Example 7) and 250 micrograms of sodium ethoxide and 40 mL of anhydrous toluene. The reaction mixture was then heated to about 80° C. and stirred at 80° C. for at least about 2 hours. The evolution of the reaction was then checked by TLC and HPLC. An additional amount of sodium ethoxide (750 micrograms) was added and the mixture was maintained at about 80° C. for about 24 hours with stirring. After cooling the reaction mixture to room temperature, silica gel and 60 mL of anhydrous toluene were added to the reaction medium, which was stirred for at least 1 hour at about 20° C.

The silica gel was filtered and washed twice with 2×30 mL of toluene. The filtrate and the washes were pooled and the solvents were distilled off under reduced pressure (T≦50° C.) until the residue solution had a volume of about 150 mL. The residue was cooled down to about 25° C. to result in 150 mL toluenic solution of ethyl 2-(6-acetamidochroman-2-yl)acetate.

Example 10
Production of ethyl 2-(6-aminochroman-2-yl)acetate

To the toluenic solution of Example 9, above, was added 6 mg of trifluoro acetic acid (48 mole). The solution was then heated up to about 60° C. for at least one hour. The solution was cooled down to about 40° C. and the solvents were distilled off (T≦50° C.) under reduced pressure until the volume of the residue was about 60 mL L.

The mixture was cooled down to room temperature and 10% (w/w) aqueous sodium hydrogen carbonate was slowly added until the pH was above 7. The solution was stirred for at least 15 minutes. The organic and aqueous layers were separated and the aqueous layer was extracted twice with 15 mL of toluene. The combined organic layers were distilled off under reduced pressure (T<50° C.) until the residue was about 35 mL L (toluenic solution of ethyl 2-(6-aminochroman-2-yl)acetate).

$^1$H-NMR (400 MHz, CDCl$_3$) 6.61 (d, J=8.9 Hz, 1H), 6.46 (dd, J=8.9 Hz, 2.5 Hz, 1H), 6.40 (d, J=2.5 Hz, 1H), 4.37 (qd, J=7.5 Hz, 1.2 Hz, 1H), 4.18 (q, J=7.2 Hz, 2H), 3.22 (s, 2H), 2.81 (ddd, J=16.5 Hz, 5.2 Hz, 4.1 Hz, 1H), 2.58 (dd, J=15.4 Hz, 7.4 Hz, 1H), 2.02 (dm, J=13.5 Hz, 1H), 1.75 (m, 1H), 1.07 (t, J=7.2 Hz, 3H).

$^{13}$C-NMR (100 MHz, CDCl$_3$) 107.9, 147.5, 139.4, 122.1, 117.3, 115.9, 115.0, 72.1, 60.6, 40.6, 27.3, 24.5, 14.2.

The procedures above may be altered or supplemented to provide other esters, salts of the compounds formed, and the like. Procedures for making other esters, either directly or through transesterification, are known in the art, as are procedures for making salts of the compounds (e.g. precipitating the salt from an organic solvent with added HCl). Additionally, the esters may be hydrolyzed to provide the free acid.

In view of the above description it is believed that one of ordinary skill can practice the methods disclosed herein. The examples given above are non-limiting in that one of ordinary skill in view of the above will readily envision other obvious permutations and variations without departing from the principal concepts embodied therein. Such permutations and variations are also within the scope of the disclosure.

What is claimed is:

1. A process for making a compound according to the formula

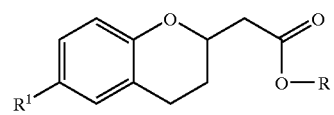

wherein R is H or an alkyl group, and R$^1$ is an amino group, an amino with a protecting group, or a nitro group, comprising:

(a) reacting a compound of the formula:

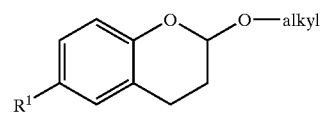

with a base under anhydrous conditions followed by adding a proton donor to produce a 2-hydroxy chromane compound of the formula:

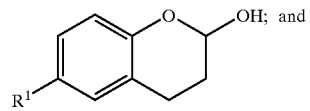

(b) condensing the hydroxychromane compound of (a) with a nucleophilic carbon species to afford the acetate compound as follows:

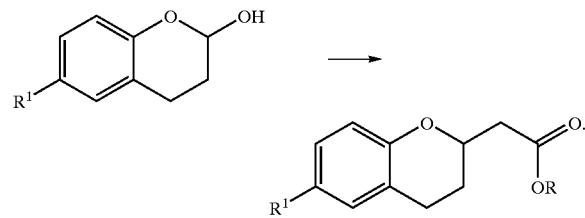

2. The process according to claim 1, wherein the base in step a) is sodium alkoxide or potassium alkoxide.

3. The process according to claim 1, wherein the proton donor in step a) is water or a mineral acid.

4. The process according to claim 1, wherein the nucleophilic carbon species in step b) is a phosphorus ylide and step b) is run in an anhydrous solvent in the presence of base.

5. The process according to claim 4, wherein the phosphorus ylide is (carbethoxymethylene)triphenylphosphine.

6. The process according to claim 1, further comprising:
(c) hydrogenating the nitro group or removing the protecting group from the amino group and forming a salt of the 6-amino group thereof;
(d) removing the alkyl group from the ester; and
(e) forming a halide salt of the 6-amino group and isolating the salt as a polymorphic or crystalline material.

7. The process according to claim 1, for making a compound according to the formula:

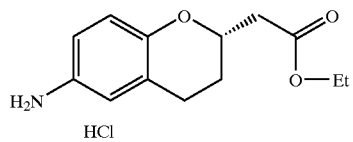

HCl in greater than 95% enantiomeric purity with respect to the corresponding (2R) enantiomer, further comprising:
(e) resolving the racemate; and
(f) forming the hydrochloride salt of the resolved amine compound.

8. The process according to claim 7, wherein the racemate comprises a nitro compound or an amine compound.

9. The process according to claim 8, comprising resolution occurring with an enzyme by an enzymatic cleavage of one enantiomer over the other enantiomer.

10. The process according to claim 9, wherein the enzyme is lipase.

11. The process according to claim 7, comprising resolution occurring by hydrolyzing the ester to a carboxylic acid, reacting the carboxylic acid with a chiral reagent to form a salt; and precipitating the salt of one enantiomer; thereby separating one enantiomer over the other enantiomer.

12. The process according to claim 11, further comprising freeing the chiral reagent and esterifying the carboxylic acid after resolution.

13. The process according to claim 1, wherein the compound according to the formula:

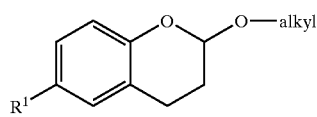

wherein $R^1$ is an amino group, an amino group with a protecting group, or a nitro group, is obtained by a scheme comprising steps:
(i) reacting a compound of the formula:

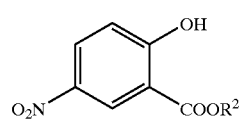

wherein $R^2$ is hydrogen or alkyl, with a reducing agent to produce a compound of the formula:

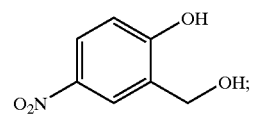

(ii) halogenating the hydroxyl group of the hydroxymethyl group; and
(iii) condensing the compound of step (ii) with an alkylvinyl ether, thereby making a compound of the formula:

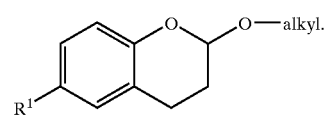

14. The process according to claim 13, wherein the reducing agent of step (i) is a chemical selected from the group consisting of lithium aluminum hydride, sodium borohydride, borane, 9-BBN, and DIBAL-H.

15. The process according to claim 13, wherein the reagent to perform the halogenation of step (ii) is thionyl chloride.

16. The process according to claim 13, wherein the alkylvinyl ether is ethylvinyl ether, thereby making a compound of the formula:

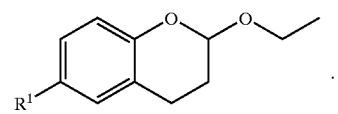

17. The process according to claim 1, wherein the compound according to the formula:

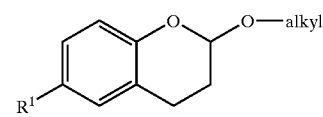

wherein $R^1$ is an amino group, an amino group with a protecting group, or a nitro group, is obtained by a scheme comprising steps:
(i) reacting a compound of the formula:

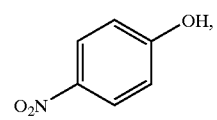

with formaldehyde, dimethylacetal, and hydrochloric acid to form a compound of the formula:

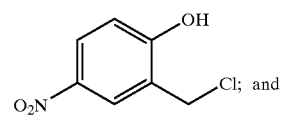

(ii) condensing the compound of step j) with an alkylvinyl ether to make a compound of the formula:

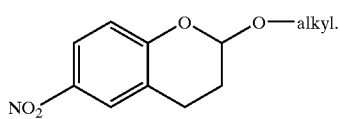

18. The process according to claim 17, wherein the alkylvinyl ether is ethylvinyl ether, thereby making a compound of the formula:

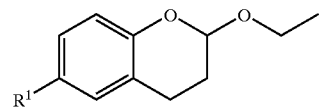

19. The process according to claim 1, further comprising (c) hydrogenating the nitro group or removing the protecting group from the amino group and forming a salt of the 6-amino group.

20. The process according to claim 19, further comprising (d) removing the alkyl group from the ester.

21. The process according to claim 17, further comprising (iii) hydrogenating the nitro group to form an amino group and adding a protecting group to the resulting amino group.

* * * * *